US006194439B1

(12) United States Patent
Dow

(10) Patent No.: US 6,194,439 B1
(45) Date of Patent: Feb. 27, 2001

(54) TRICYCLIC POLYHYDROXYLIC TYROSINE KINASE INHIBITORS

(75) Inventor: Robert L. Dow, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 08/142,284

(22) PCT Filed: Apr. 10, 1992

(86) PCT No.: PCT/US92/02799

§ 371 Date: Nov. 23, 1993

§ 102(e) Date: Nov. 23, 1993

(87) PCT Pub. No.: WO92/21660

PCT Pub. Date: Dec. 10, 1992

Related U.S. Application Data

(63) Continuation of application No. 07/706,629, filed on May 29, 1991, now abandoned.

(51) Int. Cl.$^7$ .......................... A61K 31/44; A61K 31/40; C07D 401/00; C07D 209/82
(52) U.S. Cl. ...................... 514/339; 514/411; 546/276.7; 548/440; 548/443; 548/444; 548/445
(58) Field of Search ............................. 58/443, 444, 440, 58/445; 514/411, 339; 546/272, 276.7

(56) References Cited

U.S. PATENT DOCUMENTS

| | | | |
|---|---|---|---|
| 2,823,158 | 2/1958 | Lo ........................................ | 514/411 |
| 2,944,058 | * 7/1960 | Kallischnigg ........................ | 546/185 |
| 3,154,556 | * 10/1964 | Freed .................................. | 546/272 |
| 3,862,952 | * 1/1975 | Berger ................................. | 546/302 |
| 3,932,424 | 1/1976 | Albrecht ............................... | 546/187 |
| 4,057,640 | 11/1977 | Biere ................................... | 514/411 |
| 4,226,774 | * 10/1980 | Gurien ................................. | 548/444 |
| 4,332,723 | * 6/1982 | Fleming .............................. | 548/444 |

FOREIGN PATENT DOCUMENTS 341905    1/1931    (GB) .

OTHER PUBLICATIONS

Carolyn Kruse, *J Med Chem*, vol. 31, pp. 1768–1772, 1988.*
Drugs of the Future 11, (1986) pp. 1029–1033.
Arch. Pharmacol. 317, (1981) pp. 100–102.
J. Nat. Product 52, (1989) pp. 1252–1257.
Biochem. Biophys. Res. Comm. 165 (1989) pp. 241–245.
J. Nat. Products 52, (1989) pp. 982–986, R.L. Geahlen.
Burger, Medicinal Chemistry 3rd Ed. Wiley Interscience, N.Y. (1970) p. 51.
Chowdhury et al., Curr. Sci. (India) vol. 47, 490–1 (1978).
Shiskina et al., Chem. Abstr. vol. 75, Entry 7377k, (1971).
Langendden et al., Chem Abstr. vol. 109, Entry 110255 (1988) abstracting EP 257,701.
Worthy, Chem. and Eng. News, pp. 27–29 (Sep. 27, 1991).
Barnes et al., J. Org. Chem., vol. 26, No. 11, (1961) pp. 4544–4548.
Horner et al., Liebigs Annalen der Chemie, vol. 5, (1973) pp. 910–935.
Patent Abst. of Japan, vol. 5, 195, (1981) Abstracting JP,A,56118069 (Yuichi), (1981).
Chem. Abst., vol. 115, No. 25, p. 993, abst. No. 279813d (1991) Abstracting JP,A,02304080 (TOYO Pharmar Co., Ltd et al.), (1990).
Van Heerden et al., J. of Chem. Soc., Perkin Transaction I, (1981) pp. 2483–2490.
David et al., Chem. Abst. vol. 114, No. 3 (1991), p. 244, abst. No. 19258j Abstracting MUTAT. RES. vol. 242, No. 2, (1990), pp. 143–149.
Doyle et al., Chem. Abst., vol. 93, No. 23, (1980) p. 9, abst. No. 215211a Abstracting XENOBIOTICA vol. 10, No. 4, (1980) pp. 247–256.
Barker et al., J. Chem. Soc. Part I (1954) pp. 870–873.

* cited by examiner

*Primary Examiner*—D. Margaret Seaman
(74) *Attorney, Agent, or Firm*—Peter C. Richardson; Gregg C. Benson; A. Dean Olson

(57) ABSTRACT

Certain tricyclic polyhydroxylic compounds, and their pharmaceutically-acceptable salts, are inhibitors of tyrosine kinase enzymes, and so are useful for the control of tyrosine kinase dependent diseases (e.g., cancer, atherosclerosis).

4 Claims, No Drawings

TRICYCLIC POLYHYDROXYLIC TYROSINE KINASE INHIBITORS

This application was filed under 35 U.S.C. §371 based on PCT/US92/02799, which was filed on Apr. 10, 1992 which is a continuation of U.S. application Ser. No. 07/706,629 which was filed on May 29, 1991 and is now abandoned.

This invention relates to tricyclic polyhydroxylic compounds which are tyrosine kinase inhibitors useful for the control of cancer, atherosclerosis and angiogenic-based disorders.

BACKGROUND OF THE INVENTION

Tyrosine-specific protein kinases (tyrosine kinases) represent a family of enzymes which catalyze the transfer of the terminal phosphate of adenosine triphosphate to tyrosine residues in protein substrates. The first members of this class to be identified were tyrosine kinases associated with viral genes (termed oncogenes) which were capable of cell transformation (i.e. pp60v-src and pp98v-fps). Later it was shown that there were normal cellular counterparts (i.e. pp60c-src and pp98c-fps) to these viral gene products. A third category of tyrosine kinases to be identified are those termed the growth factor receptors, which includes insulin, epidermal growth factor, and p185HER-2 receptors. All of these tyrosine kinases are believed, by way of substrate phosphorylation, to play critical roles in signal transduction for a number of cell functions.

Though the exact mechanisms of signal transduction have yet to be elucidated, tyrosine kinases have been shown to be important contributing factors in cell proliferation, carcinogenesis and cell differentiation. Therefore, inhibitors of these tyrosine kinases are useful for the prevention and chemotherapy of proliferative diseases dependent on these enzymes.

SUMMARY OF THE INVENTION

This invention is directed to tricyclic polyhydroxylic compounds that are useful as tyrosine kinase inhibitors. The compounds of this invention have the formula

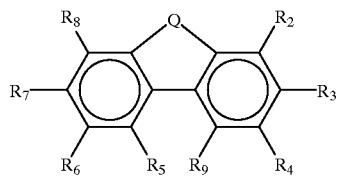

Formula I and the pharmaceutically-acceptable cationic salts and pro-drugs thereof
wherein
Q is

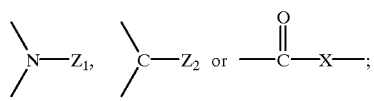

at least two and no more than four of $R_2$, $R_3$, $R_4$, $R_5$, $R_6$, $R_7$ and $R_8$ are OH, the remainder being H;

$R_9$ is H or halo, with the proviso that $R_9$ is halo only when Q is

$Z_1$ is H, benzyl, alkyl($C_1$–$C_4$), —$(CH_2)_n$—phenyl—$R_{22}$, —$(CH_2)_n$—dichlorophenyl,

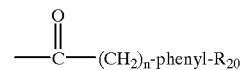

—$SO_2$—$R_{21}$, —$CH_2$—pyridyl or

wherein n is 0–3;

$R_{20}$ is H, t-butyl, $CF_3$, —$SO_2$—alkyl($C_1$–$C_4$), halo, alkyl($C_1$–$C_4$), phenyl or $NO_2$;

$R_{21}$ is phenyl, alkyl($C_1$–$C_4$), benzyl, nitrophenyl, dichlorophenyl or halophenyl;

$R_{22}$ is —C≡N, $CF_3$, phenylsulfonyl, halo or alkyl($C_1$–$C_4$);

$Z_2$ is H, =O, benzyl, hydroxylbenzyl, =N—phenyl—$R_{10}$=CH—phenyl—$R_{10}$, —$CH_2$—pyridyl, —$CH_2$—quinolyl, —$CH_2$—pyridyl, =CH—quinolyl or

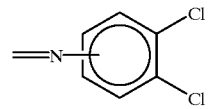

wherein
$R_{10}$ is —C≡N, H, $CF_3$, OH, $NO_2$, alkyl($C_1$–$C_4$) or —$SO_2$—alkyl($C_1$–$C_4$) with the proviso that when $Z_2$ is bonded with a single bond to the carbon to which it is attached that that carbon is also bonded to a hydrogen;

X is N—$Z_3$ or O; and $Z_3$ is H, alkyl($C_1$–$C_4$), —$CH_2$phenyl—$R_{11}$ or (dichlorophenyl)methyl wherein $R_{11}$ is H, —$NO_2$,

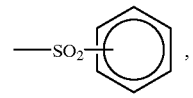

hydroxyl or halo.

A first group of preferred compounds of Formula I are compounds wherein $R_2$, $R_3$ and $R_4$ are H or OH; $R_6$ and $R_7$ are OH; $R_5$ and $R_8$ are H; $R_9$ is H or halo;
Q is

$Z_1$ is H, benzyl, alkyl($C_1$–$C_4$), —$(CH_2)_n$—phenyl—$R_{22}$, —$(CH_2)_n$—dichlorophenyl,

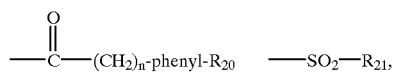

—CH$_2$—pyridyl, and

wherein n is 0–3;

$R_{20}$ is H, t-butyl, CF$_3$, —SO$_2$—alkyl(C$_1$–C$_4$), halo, alkyl (C$_1$–C$_4$), phenyl or NO$_2$;

$R_{21}$ is phenyl, alkyl(C$_1$–C$_4$), benzyl, nitrophenyl, dichlorophenyl or halophenyl; and $R_{22}$ is —C≡N, CF$_3$, phenylsulfonyl, halo or alkyl (C$_1$–C$_4$).

A first group of especially preferred compounds within this first preferred group of Formula I compounds are compounds wherein $R_2$, $R_3$, $R_6$ and $R_7$ are OH; $R_5$ and $R_8$ are H; and $R_9$ is H or halo. A second group of especially preferred compounds within this first preferred group of Formula I compounds are compounds wherein $R_3$, $R_4$, $R_6$, $R_7$ are OH; $R_2$, $R_5$, $R_8$ and $R_9$ are H; and $Z_1$ is H,

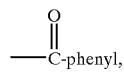

benzyl, —alkyl(C$_1$–C$_4$), —SO$_2$—phenyl, —SO$_2$—alkyl(C$_1$–C$_4$) and —CH$_2$—3-pyridyl. A third group of especially preferred compounds within this first preferred group of Formula I compounds are compounds wherein $R_2$, $R_3$, $R_4$, $R_5$, $R_8$ and $R_9$ are H; $R_6$ and $R_7$ are OH; and $Z_1$ is H or

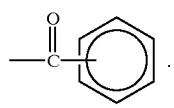

A second group of preferred compounds of Formula I are compounds wherein

Q is

$Z_2$ is H, =O, benzyl, hydroxybenzyl, =N—phenyl—$R_{10}$, =CH—phenyl—$R_{10}$, —CH$_2$—pyridyl, —CH$_2$—quinolyl, =CH$_2$—pyridyl, —CH—quinolyl or

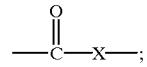

and $R_{10}$ is —C≡N, H, CF$_3$, OH, NO$_2$, alkyl(C$_1$–C$_4$) and —SO$_2$—alkyl(C$_1$–C$_4$).

A first group of especially preferred compounds within this second preferred group of Formula I compounds are compounds wherein $R_3$, $R_4$, $R_6$ and $R_7$ are OH and $R_2$, $R_5$, $R_8$ are H.

A second group of especially preferred compounds within this second group of preferred Formula I compounds are compounds wherein $R_3$, $R_4$, $R_7$ and $R_8$ are OH and $R_2$, $R_5$ and $R_6$ are H.

A third group of especially preferred compounds within this second preferred group of Formula I compounds are compounds wherein $Z_2$ is H or =O; $R_6$ and $R_7$ are OH; and $R_2$, $R_3$, $R_4$, $R_5$ and $R_8$ are H.

A fourth group of especially preferred compounds within this second preferred group of Formula I compounds are compounds wherein $Z_2$ is =O, benzyl, H, —CH$_2$—4-pyridyl, —CH$_2$—4-quinolyl, =CH—4-pyridyl, =CH—4-quinolyl or =CH—phenyl; $R_7$ and $R_8$ are OH; and $R_2$, $R_3$, $R_4$, $R_5$ and $R_6$ are H.

A third group of preferred compounds are compounds of formula I wherein Q is $$—\overset{O}{\underset{\|}{C}}—X—;$$

$Z_3$ is H, alkyl(C$_1$–C$_4$), —CH$_2$—phenyl—$R_{11}$ or (dichlorophenyl)methyl; and $R_{11}$ is H, —NO$_2$,

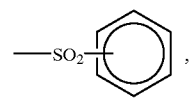

hydroxyl or halo. A first group of especially preferred compounds within this third preferred group are compounds wherein X is —O—; and $R_5$ is H. A second group of especially preferred compounds within this third preferred group are compounds wherein X is N—$Z_3$; $R_3$, $R_4$, $R_6$ and $R_7$ are OH; and $R_2$, $R_5$ and $R_8$ are H. A third group of especially preferred compounds within this third preferred group are compounds wherein X is N—$Z_3$; $R_3$, $R_4$, $R_7$ and $R_8$ are OH; and $R_2$, $R_5$ and $R_6$ are H. A fourth group of especially preferred compounds within this third preferred group are compounds wherein X is N—$Z_3$; $Z_3$ and $R_5$ are H; and any two $R_2$, $R_3$, $R_4$, $R_6$, $R_7$ and $R_8$ are OH.

The present invention is also directed to pharmaceutical compositions for the control of tyrosine kinase dependent diseases in mammals which comprise a compound of the formula I in a pharmaceutically-acceptable carrier; and to a method of controlling tyrosine kinase dependent diseases which comprises administering to a mammal suffering from tyrosine kinase dependent diseases a tyrosine kinase dependent disease controlling amount of a compound of the formula I or ellagic acid.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The expression "prodrug" refers to compounds which are drug precursors which, following administration and absorption, release the drug in vivo via some metabolic process. Exemplary prodrugs are alkyl ethers and acyl esters of the phenolic compounds such as methylether, esters of alkanoic ($C_1$–$C_{10}$)acids, and acids of the formula

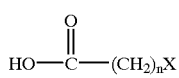

wherein n is 1 to 6 and X is an amino or carboxyl (acid, ester) group, and the formula

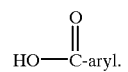

Other features and advantages will be apparent from the specification and claims.

DETAILED DESCRIPTION OF THE INVENTION

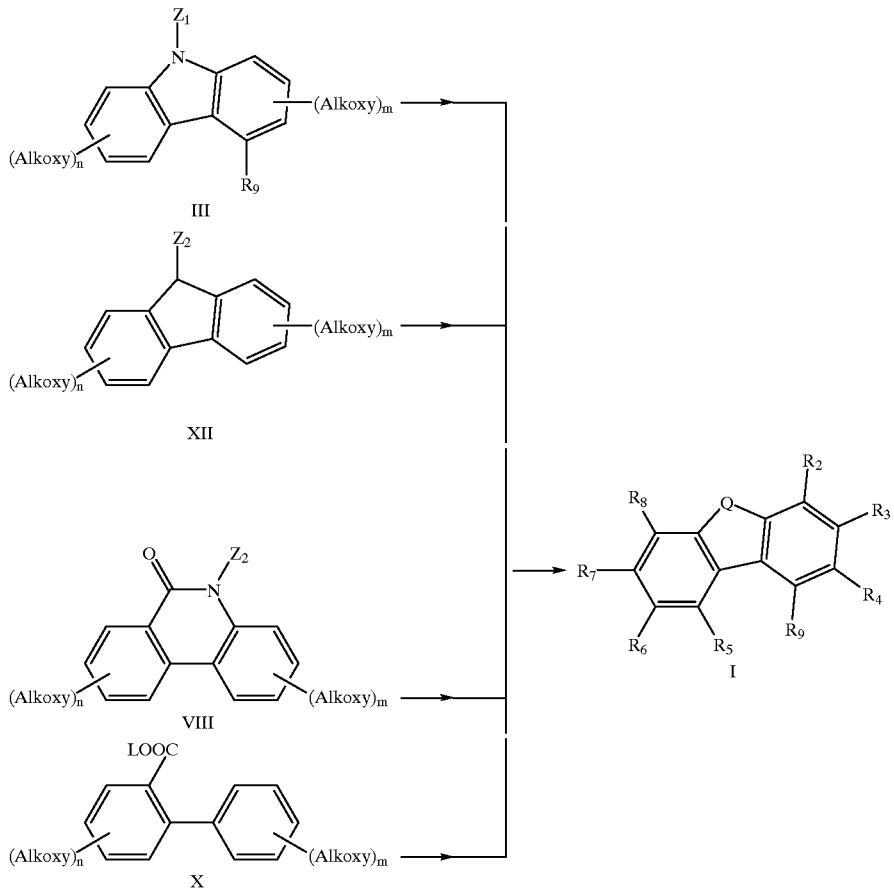

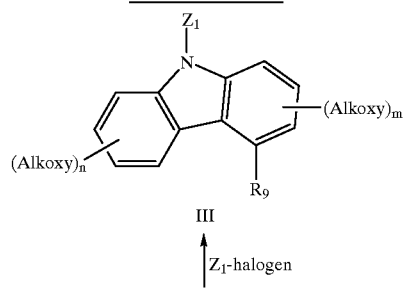

7
-continued
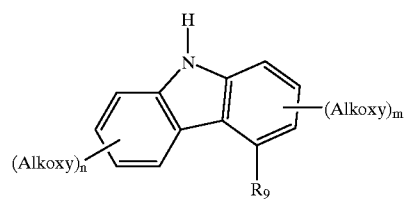
IV
↑
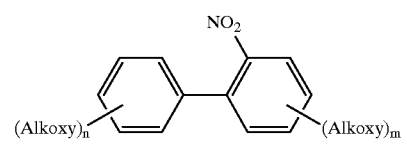
V
↑
8
-continued
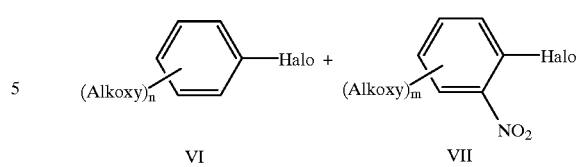
VI    VII
Reaction Scheme III
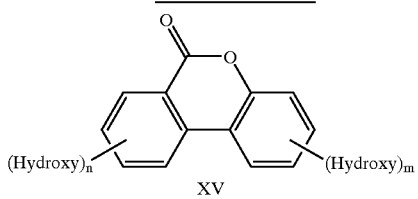
XV
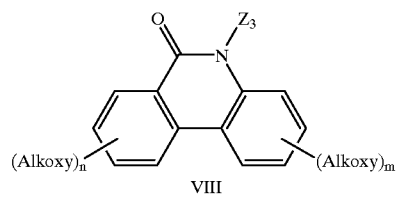
VIII
↑ $Z_3$-halogen
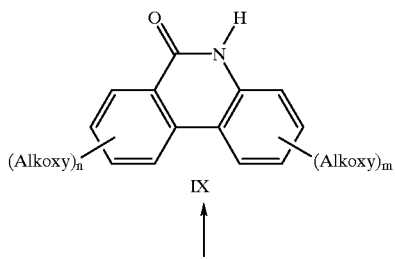
IX
↑
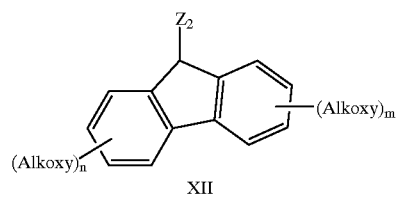
XII
↑ Amine
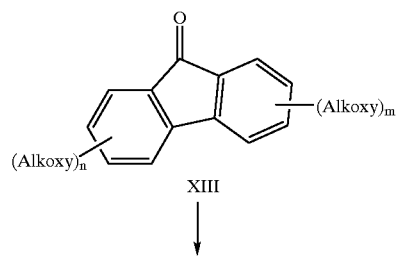
XIII
↓
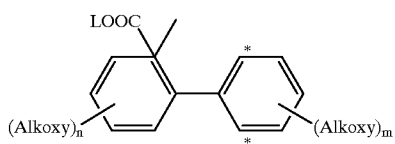
X
↑
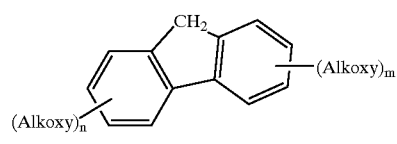
XX
↓ $Z_2$—CHO

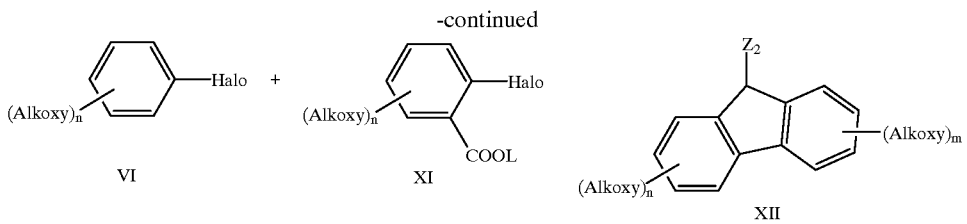

Ellagic acid is a natural product and is available from Aldrich Co. Its preparation is disclosed in Annual Drug Data Report 1986, 978 and Drugs of the Future 1986, 11, 1029.

According to Reaction Scheme I the desired Formula I compounds wherein Q and $R_2$–$R_9$ are as defined above may be prepared by deprotecting the appropriate formula III, XII and VIII compounds wherein

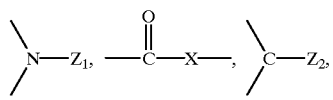

and $R_9$ are as defined above and n+m is at least two and no more than four. Alkoxy is defined as $C_1$–$C_4$.

The deprotection is generally performed in a non-hydroxylic solvent (that is preferably non-coordinating with the below described demethylating agent) preferably a chlorinated solvent such as carbon tetrachloride or methylene chloride. A demethylating agent such as boron tribromide, trialkylsilylhalides, is added to the formula III, XII or VIII compound solution at a temperature of about 0° C. to about 80° C. for about 1 hour to about 24 hours at pressures of about 0.1 psi to about 50 psi although typically the reaction is conducted at ambient pressures. Alternatively these demethylations can be run in aqueous HBr at a temperature of about 50° C. to 100° C. using the above pressures and times. Typically, a ratio of about 2 to about 5 equivalents of boron tribromide to the Formula III, XII or VII compound is used. Preferably, the reaction is performed in dichloromethane with boron tribromide at ambient temperature and pressure for 2 to 24 hours.

In addition, according to Reaction Schemes I and III the desired Formula I compounds wherein Q is

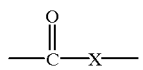

(i.e. Formula XV compounds); X is —O—; and n and m are as defined above; are prepared by deprotection/cyclization of Formula X compounds wherein n and m are as defined above; O-L is an appropriate leaving group (e.g. alkoxy or phenoxy); and having a suitably disposed alkoxy group(s) (e.g. asterisk positions). Generally this deprotection/cyclization is performed in a corollary fashion to the above described deprotection of Formula III, XII or VIII compounds to Formula I compounds.

According to Reaction Schemes I and II, Formula III compounds wherein $R_9$, n and m are as defined above may be prepared by alkylation/acylation of the appropriate Formula IV compounds wherein n, m and $R_9$ are as defined above with the appropriate $Z_1$-halogen compound.

Generally, the Formula IV compounds are exposed to a strong base such as metal hydrides, alkylamine metals or metal alkoxides at temperatures of —70° C. to about ambient in a polar aprotic solvent such as ethereal solvents DMF or DMSO solvents. The appropriate $Z_1$-halogen compound is added to the above solution at a temperature of about –70° C. to about 50° C. for about 1 to 24 hours.

According to Reaction Scheme II, Formula IV compounds wherein n, m are as defined above and $R_9$ is H may be prepared by cyclizing the appropriate Formula V compounds. Typically the cyclization occurs in the presence of a deoxygenating agent such as a trialkylphosphite at temperatures of ambient to 200° C. preferably in an inert atmosphere such as nitrogen over 5 to 24 hours.

In a corollary fashion, for those Formula IV compounds wherein $R_9$ is halogen, the appropriate Formula V compound is first reacted with the appropriate halogen prior to the above cyclization. Generally the Formula V compound is exposed to the halogen in a suitable solvent at ambient temperatures and pressures (i.e. typical halogenation conditions).

According to Reaction Scheme II, Formula V compounds wherein n and m are as defined above may be prepared by coupling the appropriate Formula VI and VII compounds wherein n and m are as defined above. Typically the Formula VI compound is metalated with an alkyl or aryl metal such as n-butyl lithium in an aprotic solvent, preferablely diethyl ether, at temperatures of –80° C. to –0° C. The resulting slurry is added to a –20° C. to ambient temperature solution of zinc halide in an ethereal solvent (preferably THF). After a half hour to two hours the resulting solution is refluxed with the appropriate Formula VII compound in the presence of a catalytic amount of a zero valent transition metal such as palladium or nickel to yield the Formula V compound.

According to Reaction Scheme I and III compounds of Formula VIII wherein $Z_3$, n and m are as defined above may be prepared by alkylating the appropriate Formula IX compounds wherein n and m are as defined above, with the appropriate $Z_3$-halogen compound.

Generally the Formula IX compounds are exposed to a base such as a metal hydride, metal alkoxide or alkylamine metal at temperatures of –70° C. to ambient in a polar aprotic solvent such as DMF, DMSO or ethereal solvent at ambient pressures. The $Z_3$-halogen compound is added to the above solution at a temperature of about –70° C. to about 50° C. for about 1 to 24 hours time at ambient pressure.

According to Reaction Scheme III compounds of Formula IX wherein n and m are as defined above may be prepared by nitrating and reducing the appropriate Formula X compounds wherein n and m are as defined above and O-L is an appropriate leaving group (e.g. alkoxy, phenoxy). Typically the Formula X compound is nitrated with nitric acid under conventional nitrating conditions. The resulting compound is then reduced with, for example, zinc, iron/weak acid, palladium on carbon, hydrogen, etc. under standard reduction conditions.

According to Reaction Scheme III Formula X compounds wherein n, m and O-L are as defined above may be prepared by coupling the appropriate Formula VI and XI compounds wherein n, m and O-L are as defined above in a corollary fashion to the preparation of the Formula V compounds from Formula VI and VII compounds described earlier.

According to Reaction Schemes I and III Formula XII compounds wherein $Z_2$ is =N—phenyl—$R_{10}$; and n and m are as defined above may be prepared by iminizing the appropriate Formula XIII compounds wherein n and m are as defined above with the appropriate primary amine. Generally the Formula XIII compound and appropriate amine are reacted as an intimate mixture with an acid catalyst, preferably a Lewis acid such as boron trifluoride etherate, at elevated temperatures of 150° C. to 250° C. for 1 to 6 hours at ambient pressures.

According to Reaction Scheme III compounds of Formula XIII wherein n and m are as defined above may be prepared from Formula X compounds wherein m, n and O-L are as defined above by an acid catalysis cyclization. Generally the Formula X compounds are added to a concentrated acid solution, preferably sulfuric, at ambient temperatures for 0.5 to 4 hours.

According to Reaction Scheme III Formula XII compounds wherein $Z_2$ is benzyl, hydroxybenzyl, —$CH_2$— pyridyl or —$CH_2$—quinolyl may be prepared from the corresponding Formula XII alkylidene compound by conventional hydrogenation using for example hydrogen in the presence of a catalyst such as palladium on carbon at elevated pressures and temperatures.

The corresponding Formula XII alkylidene compounds may be prepared from Formula XIII compounds wherein n and m are as defined above by reduction to the corresponding Formula XX methylene intermediate followed by condensation with the appropriate $Z_2$—CHO aldehyde compound. Generally, the Formula XIII compounds are reduced by conventional hydrogenation using for example hydrogen in the presence of a catalyst such as palladium on carbon at elevated pressures and temperatures. The resulting Formula XX compounds are reacted in pyridine-type solvents in the presence of an alkylammonium base such as Triton B with the appropriate $Z_2$—CHO compound for 2 hours to 36 hours time at temperatures at ambient to 150° C. at ambient pressure.

The starting materials for the above described reaction schemes (e.g. Formula VI, VII and XI compounds and the reagents $Z_1$-halogen, $Z_3$-halogen, $Z_2$-CHO or amines) can be easily synthesized by those skilled in the art starting from common chemical reagents using conventional methods of organic synthesis.

The compounds of this invention are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The acyl prodrugs of the present phenolic compounds may be prepared by, for example, acylation of the tricyclic phenolic with the appropriate acid halide/anhydride in the presence of an organic amine base (e.g. pyridine, $Et_3N$).

The compounds of this invention are all readily adapted to therapeutic use as tyrosine kinase inhibitors for the control of tyrosine kinase dependent diseases in mammals. Tyrosine kinase dependent diseases refer to hyperproliferative disorders which are initiated/maintained by aberrant tyrosine kinase enzyme activity. Examples include cancer, atherosclerosis, angiogenic-based diseases (e.g., tumor growth, diabetic retinopathy), etc.

The in vitro tyrosine kinase inhibitory activity of the present compounds may be demonstrated by methods based on standard procedures. In one method the enzyme pp60src, a tyrosine-specific phosphokinase (tyrosine kinase) associated with the inner surface of the plasma membrane, is purified from Rous sarcoma virus-transformed rat cells. In the basis assay the enzyme is incubated with the substrate, va15 angiotensin II, and gamma-32p-ATP in a total volume of 25 µl for 25 minutes at 30° C. according to Wong, T. W., Goldberg, A. R., *J. Biol. Chem.*, 259, 8505–8512 (1984). The reaction is terminated by the addition of 45 µl of 5% TCA, incubated on ice for 5 minutes and centrifuged for 1 minute to remove precipitated protein. 35 µl aliquots of the supernatants are applied to phospho-cellular paper circles, which are then washed in 3 changes of 0.5% H3PO4, acetone-rinsed, dried and counted by liquid scintillation. For screening, the compound to be tested is included in the 25 µl incubation mixture; compounds are tested at 10-4M, 10-5M and 10-6M and appropriate solvent controls are included in all assays.

The compounds are administered either orally or parenterally, or topically as eye drops, in dosages ranging from about 0.1 to 10 mg/kg of body weight per day in single or divided doses. Of course, in particular situations, at the discretion of the attending physician, doses outside of this range will be used.

The compounds of this invention can be administered in a wide variety of different dosage forms, i.e., they may be combined with various pharmaceutically-acceptable inert carriers in the form of tablets, capsules, lozenges, troches, hard candies, powders, sprays, elixirs, syrups, injectable or eye drop solutions, and the like. Such carriers include solid diluents or fillers, sterile aqueous media and various non-toxic organic solvents.

For purposes of oral administration, tablets containing various excipients such as sodium citrate, calcium carbonate and calcium phosphate are employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the essential active ingredient therein can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitable buffered, if necessary, and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of topical administration, dilute sterile, aqueous solutions (usually in about 0.1% to 5% concentration), otherwise similar to the above parenteral solutions, are prepared in containers suitable for dropwise administration to the eye.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

EXAMPLE 1

5-Phenylmethyl-2,3,8,9-tetrahydroxy-6(5H)-phenanthridinone—To a cooled (0° C.), stirred solution of 5-phenylmethyl-2,3,8,9-tetramethoxy-6(5H)-phenanthridinone (0.50 g, 1.23 mol) in dichloromethane (12 mL) was added boron tribromide (0.58 mL, 6.17 mmol) dropwise. The reaction mixture was allowed to stir at room temperature for 2 hours, poured into ice water and extracted with EtOAc. The organic phase was washed with water, brine, dried ($Na_2SO_4$), filtered and concentrated in vacuo. The residue was recrystallized from MeOH/$CCl_4$ to afford the title compound (0.30 g); m.p. 261–263° C. Anal. Calcd. for $C_{20}H_{15}NO_5.0.5H_2O$: C, 67.03; H, 4.50; N, 3.91. Found: C, 67.24; H, 3.91; N, 3.90.

The following compounds Examples (2–92) were prepared from the appropriate starting material using the above general procedure:

2,3,8,9-Tetrahydroxy-6(5H)-phenanthridinone; m.p. >250° C. Anal. Calcd. for $C_{13}H_9NO_5.1.3H_2O$: C, 55.14; H, 4.15; N, 4.95. Found: C, 54.83; H, 3.71; N, 4.85.

2,3,7,8-Tetrahydroxy-6(5H)-phenanthridinone; m.p. >360° C. Anal. Calcd. for $C_{13}H_9NO_5$: C, 60.25; H, 3.50; N, 5.41. Found: C, 56.76; H, 3.50; N, 4.82.

2,3-Dihydroxy-6(5H)-phenanthridinone; m.p. 112–113° C.

8,9-Dihydroxy-6(5H)-phenanthridinone; m.p. 311° C. dec. (acetone). Anal. Calcd. for $C_{13}H_9NO_3$: C, 68.72; H, 3.99; N, 6.17. Found: C, 67.98; H, 3.78; N, 5.81.

5-Phenylmethyl-2,3,7,8-tetrahydroxy-6(5H)-phenanthridinone; m.p. 224–225° C. (MeOH/$CCl_4$). Anal. Calcd. for $C_{20}H_{15}NO_5.0.75H_2O$: C, 66.20; H, 4.58; N, 3.86. Found: C, 66.52; H, 4.40; N, 3.86.

5-Ethyl-2,3,8,9-tetrahydroxy-6(5H)-phenanthridinone; m.p. 309–310° C. (MeOH/$CCl_4$). Anal. Calcd. for $C_{15}H_{13}NO_5.0.5H_2O$: C, 60.81; H, 4.76; N, 4.27. Found: C, 60.56; H, 4.98; N, 4.17.

5-Ethyl-2,3,7,8-tetrahydroxy-6(5H)-phenanthridinone; m.p. 275° C. (acetone/hexanes). Anal. Calcd. for $C_{15}H_{13}NO_5.1H_2O$: C, 59.01; H, 4.95; N, 4.59. Found: C, 58.70; H, 4.65; N, 4.38.

5-((4-Nitrophenyl)methyl)-2,3,7,8-tetrahydroxy-6(5H) phenanthridinone; m.p. 258–263° C. (MeOH/$CCl_4$). Anal. Calcd. for $C_{20}H_{14}N_2O_7.0.75H_2O$: C, 58.90; H, 3.83; N, 6.87. Found: C, 58.88; H, 3.77; N, 6.84.

5-((4-Nitrophenyl)methyl)-2,3,8,9-tetrahydroxy-6(5H)-phenanthridinone; m.p. 325° C. dec (MeOH/$CCl_4$). Anal. Calcd. for $C_{20}H_{14}N_2O_7.0.75H_2O$: C, 58.90; H, 3.83; N, 6.87. Found: C, 58.88; H, 3.32; N, 6.83.

5-((3,4-Dichlorophenyl)methyl)-2,3,7,8-tetrahydroxy-6 (5H)-phenanthridinone; m.p. 246° C. (MeOH/$CCl_4$). Anal. Calcd. for $C_{20}H_{13}Cl_2NO_5.0.5H_2O$: C, 56.23; H, 3.30; N, 3.28. Found: C, 56.51; H, 2.98; N, 3.28.

5-((3,4-Dichlorophenyl)methyl)-2,3,8,9-tetrahydroxy-6 (5H)-phenanthridinone; m.p. 318° C. (MeOH/$CCl_4$). Anal. Calcd. for $C_{20}H_{13}Cl_2NO_5.0.5H_2O$: C, 56.23; H, 3.30; N, 3.28. Found: C, 56.36; H, 2.95; N, 3.14.

5-(((4-Phenylsulfonyl)phenyl)methyl)-2,3,7,8-tetrahydroxy-6(5H)-phenanthridinone; m.p. 305–307° C. (MeOH/$CCl_4$). Anal. Calcd. for $C_{26}H_{19}NO_7S.0.5H_2O$: C, 62.65; H, 4.04; N, 2.81. Found: C, 62.53; H, 3.65; N, 2.83.

5-(((4-Phenylsulfonyl)phenyl)methyl)-2,3,8,9-tetrahydroxy-6(5H)-phenanthridinone; m.p.245–251° C. (MeOH/$CCl_4$).

5-((4-Hydroxyphenyl)methyl-2,3,8,9-tetrahydroxy-6 (5H)-phenanthridinone; m.p. 168° C. (MeOH/$CCl_4$). Anal. Calcd. for $C_{20}H_{15}NO_6.1.5H_2O$: C, 61.23; H, 4.24; N, 3.57. Found: C, 61.49; H, 4.50; N, 3.50.

5-((3-Phenyl)propyl)-2,3,8,9-tetrahydroxy-6(5H)-phenanthridinone; m.p. 155–158° C. (MeOH/$CCl_4$).

1,2-Dihydroxyfluoren-9-one; m.p. 184–185° C. (EtOAc/hexanes). Anal. Calcd. for $C_{13}H_8O_3$: C, 73.58; H, 3.80. Found: C, 73.18; H, 3.64.

2,3-Dihydroxyfluoren-9-one; m.p. 228–230° C. (EtOAc/hexanes). Anal. Calcd. for $C_{13}H_8O_3.0.25H_2O$: C, 72.81; H, 3.88. Found: C, 72.83; H, 3.84.

2,3,6,7-Tetrahydroxyfluoren-9-one; m.p. >250° C. Anal. Calcd. for $C_{13}H_8O_5.0.3H_2O$: C, 62.40; H, 3.47. Found: C, 62.17; H, 3.37.

1,2,6,7-Tetrahydroxyfluoren-9-one; m.p. 304° C. dec. (MeOH/$CHCl_3$). Anal. Calcd. for $C_{13}H_8O_5$: C, 63.95; H, 3.30. Found: C, 63.51; H, 3.12.

1,2-Dihydroxy-9H-fluorene; m.p. 159–162° C. (EtOAc/cyclohexane).

2,3-Dihydroxy-9H-fluorene; m.p. 155–156° C. (EtoAc/cyclohexane).

2,3,6,7-Tetrahydroxy-9H-fluorene; m.p. >250° C. Anal. Calcd. for $C_{13}H_{10}O_4.0.25H_2O$: C, 66.52; H, 4.51. Found: C, 66.69; H, 4.29.

9-(Phenylmethylene)-1,2-dihydroxyfluorene; m.p. 139–141° C. Anal. Calcd. for $C_{20}H_{14}O_2.0.33H_2O$: C, 82.17; H, 5.06. Found: C, 81.93; H, 4.99.

9-(Phenylmethylene)-2,3,6,7-tetrahydroxyfluorene; foam. 1H NMR ($d_6$-DMSO) delta 9.04 (br s, 1H), 9.01 (br s, 1H), 8.77 (br s, 1H), 8.61 (br s, 1H), 7.52–7.28 (m, 5H), 7.19 (s, 1H), 7.10 (s, 1H), 6.92 (s, 1H), 6.85 (s, 1H), 6.83 (s, 1H).

9-(Phenylmethyl)-2,3,6,7-tetrahydroxyfluorene; m.p. 230° C. dec. Anal. Calcd. for $C_{20}H_{16}O_4.0.25H_2O$: C, 73.95; H, 5.12. Found: C, 74.04; H, 5.02.

9-(Phenylmethyl)-1,2-dihydroxyfluorene; m.p. 134–136° C.

9-(Phenylmethyl)-1,2,6,7-tetrahydroxyfluorene; m.p. 233–235° C. (EtOAc/hexanes). Anal. Calcd. for $C_{20}H_{16}O_4.0.1H_2O$: C, 74,57; H, 5.07. Found: C, 74.45; H, 4.72.

9-((4-Hydroxyphenyl)methylene)-2,3,6,7-tetrahydroxyfluorene; m.p. 210° C. dec. Anal. Calcd. for $C_{20}H_{14}O_5$: C, 71.86; H, 4.22. Found: C, 67.66; H, 4.02.

9-((4-Hydroxyphenyl)methylene)-1,2,6,7-tetrahydroxyfluorene; m.p. 228–230° C. (MeOH/$H_2O$). Anal. Calcd. for $C_{20}H_{14}O_5.0.5H_2O$: C, 69.97; Hr 4.40. Found: C, 69.84; H, 4.30.

9-((4-Hydroxyphenyl)methyl)-2,3,6,7-tetrahydroxyfluorene; m.p. 314–316° C. Anal. Calcd. for $C_{20}H_{16}O_5.0.25H_2O$: C, 70.48; H, 4.88. Found: C, 70.26; H, 4.59.

9-((4-Pyridyl)methylene)-1,2-dihydroxyfluorene; m.p. 250° C. dec (MeOH/$CHCl_3$).

9-((4-Pyridyl)methyl)-1,2-dihydroxyfluorene; m.p. 263° C. dec.

9-((4-Pyridyl)methyl)-2,3,6,7-tetrahydroxyfluorene; m.p. 240° C. dec. (MeOH/CHCl$_3$). Anal. Calcd. for C$_{19}$H$_{15}$NO$_4$.0.5H$_2$O: C, 68.15; H, 4.97. Found: C, 68.57; H, 4.75.

9-(((4-Trifluoromethyl)phenyl)methylene)-2,3,6,7-tetrahydroxyfluorene; m.p. 228° C. Anal. Calcd. for C$_{21}$H$_{13}$F$_3$O$_4$.0.5H$_2$O: C, 63.80; H, 3.57. Found: C, 64.11; H, 3.55.

9-((4-Quinolyl)methylene)-2,3,6,7-tetrahydroxyfluorene; m.p. >320° C.

9-((4-Quinolyl)methylene)-1,2-dihydroxyfluorene; m.p. 315° C. (MeOH).

9-((4-Quinolyl)methylene)-1,2,6,7-tetrahydroxyfluorene; m.p. >350° C.

9-((4-Quinolyl)methyl)-1,2-dihydroxyfluorene; m.p. 244–246° C. (MeOH/CHCl$_3$).

9-((4-Quinolyl)methyl)-2,3,6,7-tetrahydroxyfluorene; m.p. 240° C. dec.

1,2,6,7-Tetrahydroxy-9H-carbazole; m.p. >280° C. (H$_2$O). Anal. Calcd. for C$_{12}$H$_9$NO$_4$: C, 62.34; H, 3.92; N, 6.06. Found: C, 62.01; H, 3.83; N, 6.03.

2,3-Dihydroxy-9H-carbazole; m.p. 279–283° C. (MeOH/H$_2$O). Anal. Calcd. for C$_{12}$H$_9$NO$_2$: C, 72.35; H, 4.55; N, 7.03. Found: C, 72.11; H, 4.49; N, 6.97.

2,3,6,7-Tetrahydroxy-9H-carbazole; m.p. >300° C. (H$_2$O). Anal. Calcd. for C$_{12}$H$_9$NO$_4$.0.2H$_2$O: C, 61.38; H, 4.03; N, 5.97. Found: C, 61.76; H, 3.77; N, 5.98.

9-Benzoyl-1,2,6,7-tetrahydroxycarbazole; m.p. 242–243° C. (MeOH/H$_2$O). Anal. Calcd. for C$_{19}$H$_{13}$NO$_5$: C, 68.05; H, 3.91; N, 4.18. Found: C, 67.71; H, 3.68; N, 4.19.

9-Benzoyl-2,3-dihydroxycarbazole; m.p. 260–261° C. EtOH/H$_2$O). Anal. Calcd. for C$_{19}$H$_{13}$NO$_3$.0.25H$_2$O: C, 74.13; H, 4.41; N, 4.55. Found: C, 74.52; H, 4.05; N, 4.51.

9-Benzoyl-2,3,6,7-tetrahydroxycarbazole; m.p. 287–292° C. (MeOH/H$_2$O). Anal. Calcd. for C$_{19}$H$_{13}$NO$_5$.1H$_2$O: C, 64.58; H, 4.27; N, 3.96. Found: C, 64.74; H, 3.97; N, 3.94.

9-(Phenylmethyl)-1,2,6,7-tetrahydroxycarbazole; m.p. 241–246° C. (MeOH/H$_2$O). Anal. Calcd. for C$_{19}$H$_{15}$NO$_4$.0.25H$_2$O: C, 70.03; H, 4.80; N, 4.30. Found: C, 70.32; H, 4.52; N. 4.07.

9-(Phenylmethyl)-2,3,6,7-tetrahydroxycarbazole; m.p. 266–271° C. (MeOH/H$_2$O). Anal. Calcd. for C$_{19}$H$_{15}$NO$_4$.0.25H$_2$O: C, 70.03; H, 4.80; N, 4.30. Found: C, 70.02; H, 4.47; N, 4.37.

9-Methyl-2,3,6,7-tetrahydroxycarbazole; m.p. >270° C. (H$_2$O). Anal. Calcd. for C$_{13}$H$_{11}$NO$_4$.0.25H$_2$O: C, 62.51; H, 4.63; N, 5.60. Found: C, 62.56; H, 4.37; N, 5.62.

9-(Methylsulfonyl)-1,2,6,7-tetrahydroxycarbazole; m.p. 211–213° C. dec. (EtOAc/hexanes). Anal. Calcd. for C$_{13}$H$_{11}$NO$_6$S: C, 50.48; H, 3.59; N, 4.53. Found: C, 50.25; H, 3.47; N, 4.25.

9-(Methylsulfonyl)-2,3,6,7-tetrahydroxycarbazole; m.p. 278–280° C. (MeOH/H$_2$O). Anal. Calcd. for C$_{13}$H$_{11}$NO$_6$S: C, 50.48; H, 3.59; N, 4.53. Found: C, 50.58; H, 3.29; N, 4.55.

9-(Phenylsulfonyl)-1,2,6,7-tetrahydroxycarbazole; m.p. 176–178° C. (MeOH/H$_2$O). Anal. Calcd. for C$_{18}$H$_{13}$NO$_6$S.0.4H$_2$O: C, 57.02; H, 3.68; N, 3.69. Found: C, 56.70; H, 3.33; N, 3.67.

9-(Phenylsulfonyl)-2,3,6,7-tetrahydroxycarbazole; m.p. 240–241° C. (MeOH/H$_2$O). Anal. Calcd. for C$_{18}$H$_{13}$NO$_6$S.1H$_2$O: C, 55.52; H, 3.88; N, 3.59. Found: C, 55.44; H, 3.45; N, 3.36.

9-(4-t-Butylbenzoyl)-1,2,6,7-tetrahydroxycarbazole; m.p. 234–236° C. (MeOH/H$_2$O). Anal. Calcd. for C$_{23}$H$_{21}$NO$_5$: C, 70.57; H, 5.36; N, 3.58. Found: C, 70.30; H, 5.36; N, 3.59.

9-((4-Trifluoromethyl)benzoyl)-1,2,6,7-tetrahydroxycarbazole: m.p. 229–230° C. (EtOAc/hexanes). Anal. Calcd. for C$_{20}$H$_{12}$F$_3$NO$_5$.0.4H$_2$O: C, 58.51; H, 3.14; N, 3.41. Found: C, 58.77; H, 2.91; N, 3.37.

9-((4-Methylsulfonyl)benzoyl)-1,2,6,7-tetrahydroxycarbazole; m.p. 286–288° C. (acetone/CH$_2$Cl$_2$). Anal. Calcd. for C$_{20}$H$_{15}$NO$_7$S: C, 58.10; H, 3.66; N, 3.39. Found: C, 58.06; H, 3.56; N, 3.39.

9-(4-Bromobenzoyl)-1,2,6,7-tetrahydroxycarbazole; m.p. 272–278° C. (EtOAc/hexanes). Anal. Calcd. for C$_{19}$H$_{12}$BrNO$_5$: C, 55.09; H, 2.92; N, 3.38. Found: C, 54.80; H, 2.72; N, 3.64.

9-(4-Phenylbenzoyl)-1,2,6,7-tetrahydroxycarbazole; m.p. 291–294° C. (EtOAc). Anal. Calcd. for C$_{25}$H$_{17}$NO$_5$.0.25H$_2$O: C, 72.19; H, 4.24; N, 3.37. Found: C, 72.32; H, 4.02; N, 3.28.

9-(3-Phenylpropionyl)-1,2,6,7-tetrahydroxycarbazole; m.p. 223–227° C. (EtOAc/hexanes). Anal. Calcd. for C$_{21}$H$_{17}$NO$_5$: C, 69.41; H, 4.71; N, 3.86. Found: C, 69.11; H, 4.52; N, 3.84.

9-(2-Napthoyl)-1,2,6,7-tetrahydroxycarbazole; m.p. 266–270° C. (EtOAc). Anal. Calcd. for C$_{23}$H$_{15}$NO$_5$.0.15H$_2$O: C, 71.21; H, 3.97; N, 3.61. Found: C, 71.30; H, 3.88; N, 3.61.

9-(3-Nitrobenzoyl)-1,2,6,7-tetrahydroxycarbazole; m.p. 275–279° C. (EtOAc). Anal. Calcd. for C$_{19}$H$_{12}$N$_2$O$_7$: C, 60.00; H, 3.18; N, 7.36. Found: C, 59.73; H, 2.90; N, 7.22.

9-(3-Pyridylmethyl)-2,3,6,7-tetrahydroxycarbazole; m.p. 290–294° C. (MeOH/H$_2$O). Anal. Calcd. for C$_{18}$H$_{14}$N$_2$O$_4$.HBr.0.5H$_2$O: C, 52.44; H, 3.67; N, 6.80. Found: C, 52.23; H, 3.94; N, 6.83.

9-((3-Methylphenyl)methyl)-1,2,6,7-tetrahydroxycarbazole; m.p. 150–155° C. dec (EtOAc/hexanes). Anal. Calcd. for C$_{20}$H$_{17}$NO$_4$: C, 71.63; H, 5.11; N, 4.18. Found: C, 71.78; H, 5.11; N, 3.96.

9-((4-Cyanophenyl)methyl)-1,2,6,7-tetrahydroxycarbazole; m.p. 225–227° C. (MeOH/H$_2$O). Anal. Calcd. for C$_{20}$H$_{14}$N$_2$O$_4$.0.25H$_2$O: C, 68.46; H, 4.13; N, 8.00. Found: C, 68.74; H, 3.75; N, 8.40.

9-((4-Trifluoromethylphenyl)methyl)-1,2,6,7-tetrahydroxycarbazole; m.p. 266–270° C. (MeOH/H$_2$O). Anal. Calcd. for C$_{20}$H$_{14}$F$_3$NO$_4$.0.25H$_2$O: C, 60.99; H, 3.68; N, 3.56. Found: C, 60.80; H, 3.41; N, 3.62.

9-((2,6-Dichlorophenyl)methyl)-1,2,6,7-tetrahydroxycarbazole; m.p. 263–265° C. (EtOAc). Anal. Calcd. for C$_{19}$H$_{13}$Cl$_2$NO$_4$: C, 58.48; H, 3.36; N, 3.59. Found: C, 58.34; H, 3.29; N, 3.53.

9-((4-Phenylsulfonyl)phenylmethyl)-1,2,6,7-tetrahydroxycarbazole; m.p. >300° C. (EtOAc/hexanes). Anal. Calcd. for C$_{25}$H$_{19}$NO$_6$S: C, 63.09; H, 4.36; N, 2.94. Found: C, 62.92; H, 3.96; N, 3.01.

9-(4-Bromophenylmethyl)-1,2,6,7-tetrahydroxycarbazole; m.p. 249–252° C. (MeOH/H$_2$O). Anal. Calcd. for C$_{19}$H$_{14}$BrNO$_4$.0.25H$_2$O: C, 56.38; H, 3.61; N, 3.46. Found: C, 56.33; H, 3.36; N, 3.35.

9-(3-Phenylpropyl)-1,2,6,7-tetrahydroxycarbazole; m.p. 246–252° C. (MeOH/CH$_2$Cl$_2$). Anal. Calcd. for C$_{21}$H$_{19}$NO$_4$: C, 72.19; H, 5.48; N, 4.01. Found: C, 71.89; H, 5.23; N, 3.95.

9-((Phenylmethyl)sulfonyl)-1,2,6,7-tetrahydroxycarbazole; m.p. 216–218° C. (MeOH/H$_2$O). Anal. Calcd. for C$_{19}$H$_{15}$NO$_6$S: C, 59.21; H, 3.92; N, 3.64. Found: C, 59.10; H, 3.64; N, 3.77.

9-((2,5-Dichlorophenyl)sulfonyl)-1,2,6,7-tetrahydroxycarbazole; m.p. >300° C. (MeOH/H$_2$O). Anal. Calcd. for C$_{18}$H$_{11}$Cl$_2$NO$_6$S.0.25H$_2$O: C, 48.60; H, 2.60; N, 3.15. Found: C, 48.67; H, 2.45; N, 3.17.

9-((4-Nitrophenyl)sulfonyl)-1,2,6,7-tetrahydroxycarbazole; m.p. 233–234° C. (MeOH/H$_2$O). Anal. Calcd. for C$_{18}$H$_{12}$N$_2$O$_8$S.0.25H$_2$O: C, 51.36; H, 2.99; N, 6.66. Found: C, 51.16; H, 2.81; N, 6.53.

4-Bromo-1,2,6,7-tetrahydroxy-9H-carbazole; m.p. >260° C. (acetone/CH$_2$Cl$_2$). Anal. Calcd. for C$_{12}$H$_8$BrNO$_4$: C, 46.47; H, 2.60; N, 4.52. Found: C, 46.47; H, 2.62; N, 4.45.

9-((4-Trifluoromethyl)benzoyl)-4-bromo-1,2,6,7-tetrahydroxycarbazole; m.p. 228–230° C. (EtOAc/hexanes). Anal. Calcd. for C$_{20}$H$_{11}$BrF$_3$NO$_5$: C, 49.81; H, 2.30; N, 2.91. Found: C, 49.78; H, 2.10; N, 2.89.

9-((4-Methylsulfonyl)benzoyl)-4-bromo-1,2,6,7-tetrahydroxycarbazole; m.p. >280° C. (MeOH). Anal. Calcd. for C$_{20}$H$_{14}$BrNO$_7$S: C, 48.79; H, 2.87; N, 2.85. Found: C, 48.42; H, 2.84; N, 2.80.

9-(4-t-Butylbenzoyl)-4-bromo-1,2,6,7-tetrahydroxycarbazole; m.p. >280° C. (MeOH/H$_2$O). Anal. Calcd. for C$_{23}$H$_{20}$BrNO$_5$: C, 58.73; H, 4.29; N, 2.98. Found: C, 58.94; H, 4.26; N, 2.95.

9-((4-Cyanophenyl)methyl)-4-bromo-1,2,6,7-tetrahydroxycarbazole; m.p. >260° C. (MeOH/CH$_2$Cl$_2$). Anal. Calcd. for C$_{20}$H$_{13}$BrN$_2$O$_4$: C, 56.49; H, 3.08; N, 6.59. Found: C, 56.24; H, 3.09; N, 6.47.

9-(Methylsulfonyl)-4-bromo-1,2,6,7-tetrahydroxycarbazole; m.p. >270° C. (MeOH/H$_2$O). Anal. Calcd. for C$_{13}$H$_{10}$BrNO$_6$S: C, 40.22; H, 2.60; N, 3.61. Found: C, 43.32; H, 3.25; N, 3.39.

N-9H-1,2,6,7-Tetrahydroxyfluoren-9-ylidene-benzamine; m.p. 235–239° C. (isopropyl alcohol/hexane). Anal. Calcd. for C$_{19}$H$_{13}$NO$_4$.0.5H$_2$O: C, 69.51; H, 4.30; N, 4.27. Found: C, 69.26; H, 3.90; N, 4.00.

N-9H-2,3,6,7-Tetrahydroxyfluoren-9-ylidene-benzamine; m.p. 184–187° C. Anal. Calcd. for C$_{19}$H$_{13}$NO$_4$.1.25H$_2$O: C, 66.76; H, 4.57; N, 4.10. Found: C, 66.92; H, 4.33; N, 3.36.

N-9H-2,3,6,7-Tetrahydroxyfluoren-9-ylidene-(4'-cyano)benzamine; m.p. >350° C. (acetone/MeOH/H$_2$O). Anal. Calcd. for C$_{20}$H$_{12}$N$_2$O$_4$.0.25H$_2$O: C, 68.86; H, 3.61; N, 8.03. Found: C, 68.71; H, 3.33; N, 7.37.

N-9H-2,3,6,7-Tetrahydroxyfluoren-9-ylidene-(4'-trifluoromethyl)benzamine; m.p. 168–172° C. (EtOAc/cyclohexane). Anal. Calcd. for C$_{20}$H$_{12}$F$_3$NO$_4$.0.25H$_2$O: C, 61.30; H, 3.22; N, 3.58. Found: C, 61.27; H, 3.23; N, 3.34.

N-9H-1,2,6,7-Tetrahydroxyfluoren-9-ylidene-(3,5-dichloro)benzamine; m.p. 258–260° C. (EtOAc/hexanes). Anal. Calcd. for C$_{19}$H$_{11}$Cl$_2$NO$_4$: C, 58.79; H, 2.86; N, 3.61. Found: C, 58.57; H, 2.80; N, 3.53.

N-9H-1,2,6,7-Tetrahydroxyfluoren-9-ylidene-(4'-nitro)benzamine; m.p. 254–256° C. (dioxane/hexanes). Anal. Calcd. for C$_{19}$H$_{12}$N$_2$O$_6$.0.5H$_2$O: C, 61.13; H, 3.50; N, 7.51. Found: C, 61.28; H, 3.72; N, 6.82.

N-9H-1,2,6,7-Tetrahydroxyfluoren-9-ylidene-(4'-i-propyl)benzamine; m.p. 147–150° C. Anal. Calcd. for C$_{22}$H$_{19}$NO$_4$.0.5H$_2$O: C, 71.34; H, 5.44; N, 3.78. Found: C, 71.67; H, 5.44; N, 3.65.

N-9H-1,2,6,7-Tetrahydroxyfluoren-9-ylidene-(4'-methylsulfonyl)benzamine; m.p. 168° C. dec. (dioxane/hexanes). Anal. Calcd. for C$_{20}$H$_{15}$NO$_6$S: C, 60.46; H, 3.81; N, 3.53. Found: C, 58.85; H, 4.83; N, 2.75.

3,4-Dihydroxy-6H-dibenzo[b,d]pyran-6-one; m.p. 254–256° C. (EtOH).

7,8-Dihydroxy-6H-dibenzo[b,d]pyran-6-one; m.p. 185–187° C. (EtOAc/cyclohexane).

8,9-Dihydroxy-6H-dibenzo[b,d]pyran-6-one; m.p. >255° C. (EtOAc).

2,3,8,9-Tetrahydroxy-6H-dibenzo[b,d]pyran-6-one; m.p. >250° C.

3,4,8,9-Tetrahydroxy-6H-dibenzo[b,d]pyran-6-one; m.p. >250° C. (EtOH). Anal. Calcd. for C$_{13}$H$_8$O$_6$: C, 60.00; H, 3.10. Found: C, 59.66; H, 2.85.

3,4,7,8-Tetrahydroxy-6H-dibenzo[b,d]pyran-6-one; m.p. >280° C. Anal. Calcd. for C$_{13}$H$_8$O$_6$.0.25H$_2$O: C, 58.99; H, 3.23. Found: C, 59.32; H, 3.20.

PREPARATION 1

A 4,5-Dimethoxy-2-((2,4,5-trimethoxy)phenyl)benzonitrile—To a cooled (−78° C.), stirred solution of 2,4,5-trimethoxybromobenzene (6.63 g, 27.0 mmol) in ether (25 mL) was added dropwise a 2.5M solution of n-butyllithium (10.7 mL, 27 mmol) in hexanes. After 10 minutes, the slurry was allowed to warm to DOC and THF (20 mL) was added. The resulting solution was added via a cannula to a cooled (0° C.), stirred solution of fused zinc chloride (4.39 g, 32.0 mmol) in THF (50 mL) and this solution was maintained at 0° C. for 1 hour.

To a slurry of bis(triphenylphosphine)palladium (II) chloride (0.3 g, 0.4 mmol) in THF (20 ml) was added a 1M solution of diisobutylaluminum hydride (0.8 mL, 0.8 mmol) and the resulting black solution was stirred at ambient temperature for 20 minutes. A solution of 2-bromo-4,5-dimethoxybenzonitrile (5.0 g, 21 mmol) in THF (20 mL) and the solution of the organozinc reagent were added to the palladium catalyst. The resulting dark solution was refluxed for 18 hours, diluted into EtOAc, washed with brine, dried (Na$_2$SO$_4$), filtered and concentrated in vacuo to afford a dark oil. Flash chromatography (30% EtOAc/hexanes) afforded the title compound (4.0 g); m.p. 154–156° C. (EtOH). Anal. Calcd. for C$_{18}$H$_{19}$NO$_5$: C, 65.65; H, 5.82; N, 4.25. Found: C, 65.28; H, 5.78; N, 3.42.

The following compounds (B–H) were prepared using the above general procedure:

Methyl 2,3-dimethoxy-6-((3,4,5-trimethoxy)phenyl)benzoate; m.p. 94–97° C. Anal. Calcd. for C$_{19}$H$_{22}$O$_7$: C, 62.97; H, 6.12. Found: C, 63.09; H, 6.05.

Ethyl 2-((3,4-dimethoxy)phenyl)-4,5-dimethoxybenzoate; m.p. 91–94° C. Anal. Calcd. for C$_{19}$H$_{22}$O$_6$: C, 65.88; H, 6.40. Found: C, 65.72; H, 6.45.

Ethyl 2,3-dimethoxy-6-((3,4-dimethoxy)phenyl)benzoate; m.p. 76–77° C. (acetone/hexanes). Anal. Calcd. for C$_{19}$H$_{22}$O$_6$: C, 65.88; H, 6.40. Found: C, 65.98; H, 6.15.

2-((3,4-Dimethoxy)phenyl)-4,5-dimethoxynitrobenzene; m.p. 149–151° C. (EtOH). Anal. Calcd. for C$_{16}$H$_{17}$NO$_6$: C, 60.18; H, 5.37; N, 4.39. Found: C, 60.27; H, 5.35; N, 4.39.

4,5-Dimethoxy-2-phenylnitrobenzene; m.p. 113–115° C. (MeOH/H$_2$O). Anal. Calcd. for C$_{14}$H$_{13}$NO$_4$: C, 64.86; H, 5.50; N, 5.40. Found: C, 64.88; H, 5.061 N, 5.29.

Ethyl 2-((3,4-dimethoxy)phenyl)benzoate; m.p. 71–75° C.

Methyl 2,3-dimethoxy-6-((2-methoxy)phenyl)benzoate; m.p. oil. Rf (silica)=0.43 (30% ethyl acetate/hexanes).

PREPARATION 2

(2,3-Dimethoxy)phenyl 2-bromo-4,5-dimethoxybenzoate—To a stirred solution of 2-bromo-4,5-dimethoxybenzoyl chloride (5.4 g, 21 mmol) in $CH_2Cl_2$ (50 mL) was added triethylamine (5.9 mL, 42 mmol) and 2,3-dimethoxyphenyl (5.4 mL, 25 mmol) dropwise over 5 minutes. The reaction was stirred for 2 hours, diluted into EtOAc, washed with brine, dried ($Na_2SO_4$), filtered and concentrated in vacuo. The resulting solids were recrystallized from EtOH to afford the title compound as a colorless solid (6.2 g); m.p. 103–105° C.

PREPARATION 3

3,4,8,9-Tetramethoxy-6H-dibenzo[b,d]pyran-6-one—A stirred mixture of (2,3-Dimethoxy)phenyl 2-bromo-4,5-dimethoxybenzoate (5.0 g, 13 mmol), sodium acetate (2.1 go 25 mmol) and bis(triphenylphosphine)palladium (II) chloride (0.9 g, 1.3 mmol) in N,N-dimethylacetamide (75 mL) was maintained at 120° C. for 23 hours. The reaction mixture was cooled, poured onto brine, acidified (pH=1) with 1N HCl and extracted with EtOAc. The organic layer was washed with brine, dried ($Na_2SO_4$), filtered and concentrated in vacuo. The resulting solids were recrystallized from EtOAc to afford the title compound (0.8 g); m.p. 222–223° C.

PREPARATION 4

A

Ethyl 4,5-dimethoxy-2-((4,5-dimethoxy-2-nitro)phenyl)benzoate—To a stirred solution of ethyl 2-((3,4-dimethoxy)phenyl)-4,5-dimethoxybenzoate (2.00 g, 5.77 mmol) in glacial acetic acid (30 mL) was added concentrated nitric acid (0.72, 11.5 mmol) dropwise. After 10 minutes, the reaction mixture was poured onto ice (150 g) and the solids were extracted into EtOAc. The organic phase was washed with water, 1N NaOH, brine, dried ($Na_2SO_4$), filtered and concentrated in vacuo to afford the title compounds as a yellow solid (2.25 g); m.p. 126–128° C. Anal. Calcd. for $C_{19}H_{21}NO_8$: C, 58.30; H, 5.41; N, 3.58. Found: C, 57.80; H, 5.40; N, 3.71.

The following compounds (B–C) were prepared from the appropriate starting material using the above general procedure:

Ethyl 2,3-dimethoxy-6-((4,5-dimethoxy-2-nitro)phenyl)benzoate; m.p. 118–120° C. Anal. Calcd. for $C_{19}H_{21}NO_8$: C, 58.30; H, 5.41; N, 3.58. Found: C, 58.28; H, 5.28; N, 3.49.

Ethyl 2-(((4,5-dimethoxy)-2-nitro)phenyl)benzoate.

PREPARATION 5

A 2,3,8,9-Tetramethoxy-6(5H)-phenanthridinone—To a stirred, heated (100° C.) slurry of iron dust (325 mesh, 2.8 g) in glacial acetic acid (30 mL) was added a solution of ethyl 4,5-dimethoxy-2-((4,5-dimethoxy-2-nitro)phenyl)benzoate (1.42 g, 3.63 mmol) in glacial acetic acid (40 mL) was added over 5 minute period. After 1.5 hours, the residual iron fillings were removed with a magnetic stir bar and the reaction slurry was poured onto ice/water (150 mL). The solids were filtered, washed with water, air-dried and dried in vacuo at 80° C. to afford the title compound as a gray solid (1.00 g); m.p. >250° C.

The following compounds (B–C) were preapred from the appropriate starting material using the above general procedure:

2,3-Dimethoxy-6(5H)-phenanthridinone; m.p. 253–255° C. (acetone/cyclohexane).

2,3,7,8-Tetramethoxy-6(5H)-phenanthridinone; $^1$H NMR ($d_6$-DMSO) delta 8.10 (d, 1H), 7.62 (s, 1H), 7.47 (d, 1H), 6.81 (s, 1H), 3.86 (s, 3H), 3.82 (s, 3H), 3.75 (s, 3H), 3.73 (s, 3H).

PREPARATION 6

A

5-Phenylmethyl-2,3,8,9-tetramethoxy-6(5H)-phenanthridinone—To a slurry of 2,3,8,9-Tetramethoxy-6(5H)-phenanthridinone (0.6 g, 1.9 mmol) in anhydrous dimethyl sulfoxide (10 mL) was added potassium t-butoxide (0.32 g, 2.85 mmol) and the resulting brown solution was stirred at room temperature for 15 minutes. After the addition of benzyl bromide (0.6 g, 3.8 mmol), the reaction mixture was allowed to stir for 1 hour. The reaction was poured into 1N HCl and extracted with EtOAc. The organic phase was washed with water, brine, dried ($Na_2SO_4$), filtered and concentrated in vacuo. The residue was flash chromatographed (30% EtOAc/hexanes) to afford the title compound (0.54 g); m.p. 214–215° C. ($CHCl_3$/hexanes). Anal. Calcd. for $C_{24}H_{23}NO_5$: C, 71.10; H, 5.72; N, 3.46. Found: C, 69.15; H, 5.65; N, 3.25.

The following compounds (B–L) were prepared from the appropriate starting material using the above general procedure:

5-Ethyl-2,3,8,9-tetramethoxy-6(5H)-phenanthridinone; m.p. 191–192° C. Anal. Calcd. for $C_{19}H_{21}NO_5$: C, 66.47; H, 6.17; N, 4.08. Found: C, 65.96; H, 6.31; N, 4.03.

5-((3,4-Dichlorophenyl)methyl)-2,3,8,9-tetramethoxy-6(5H)-phenanthridinone; 225–226° C. Anal. Calcd. for $C_{24}H_{21}Cl_2NO_5$: C, 60.78; H, 4.46; N, 2.95. Found: C, 60.44; H, 4.29; N, 2.95.

5-(((4-Phenylsulfonyl)phenyl)methyl)-2,3,8,9-tetramethoxy-6(5H)-phenanthridinone; m.p. 245–246° C. ($CHCl_3$/MeOH). Anal. Calcd. for $C_{30}H_{27}NO_7S$: C, 66.04; H, 4.99; N, 2.57. Found: C, 65.56; H, 4.75; N, 2.59.

5-((4-Nitrophenyl)methyl)-2,3,8,9-tetramethoxy-6(5H)-phenanthridinone; m.p. 239–240° C. Anal. Calcd. for $C_{24}H_{22}N_2O_7$: C, 64.00; H, 4.92; N, 6.22. Found: C, 63.66; H, 4.71; N, 6.16.

5-((4-Methoxyphenyl)methyl-2,3,8,9-tetramethoxy-6(5H)-phenanthridinone; m.p. 199–200° C. Anal. Calcd. for $C_{25}H_{25}NO_6$: C, 70.58; H, 5.92; N, 3.29. Found: C, 68.16; H, 5.54; N, 3.17.

5-Ethyl-2,3,7,8-tetramethoxy-6(5H)-phenanthridinone; m.p. 139–141° C. Anal. Calcd. for $C_{19}H_{21}NO_5$: C, 66.47; H, 6.17; N, 4.08. Found: C, 66.13; H, 6.03; N, 3.98.

5-Phenylmethyl-2,3,7,8-tetramethoxy-6(5H)-phenanthridinone; m.p. 183–184° C. (acetone/cyclohexane). Anal. Calcd. for $C_{24}H_{23}NO_5$: C, 71.10; H, 5.72; N, 3.46. Found: C, 70.86; H, 5.68; N, 3.40.

5-((4-Nitrophenyl)methyl)-2,3,7,8-tetramethoxy-6(5H)-phenanthridinone; m.p. 191–193° C. Anal. Calcd. for $C_{24}H_{22}N_2O_7$: C, 64.00.; H, 4.92; N, 6.22. Found: C, 63.65; H, 4.65; N, 6.30.

5-((3,4-Dichlorophenyl)methyl)-2,3,7,8-tetramethoxy-6(5H)-phenanthridinone; m.p. 172–173° C. Anal. Calcd. for $C_{24}H_{21}Cl_2NO_5$: C, 60.78; H, 4.46; N, 2.95. Found: C, 60.66; H, 4.52; N, 2.92.

5-(((4-Phenylsulfonyl)phenyl)methyl)-2,3,7,8-tetramethoxy-6(5H)-phenanthridinone; m.p. 189–191° C. Anal. Calcd. for $C_{30}H_{27}NO_7S$: C, 66.04; H, 4.99; N, 2.57. Found: C, 64.31; H, 4.70; N, 2.60.

5-((3-Phenyl)propyl)-2,3,8,9-tetramethoxy-6(5H)-phenanthridinone; m.p. 209–211° C. (chloroform/MeOH). Anal. Calcd. for $C_{26}H_{27}NO_5$: C, 72.05; H, 6.28; N, 3.23. Found: C, 71.38; H, 6.03; N, 3.20.

PREPARATION 7

A 2,3,6,7-Tetramethoxy-fluoren-9-one—Ethyl 2-((3,4-dimethoxy)phenyl)-4,5-dimethoxybenzoate (2.25 g, 6.50 mmol) was added to a stirred mixture of concentrated sulfuric acid/water (93:7 v/v, 30 mL) producing a slightly exothermic reaction. The resulting green solution was stirred at ambient temperature for 1 hour. The reaction solution ws poured onto ice (70 g) and extracted with EtOAc. The organic phase was washed with saturated aqueous sodium bicarbonate, brine, dried ($Na_2SO_4$), filtered and concentrated in vacuo to afford orange solids. The solids were recrystallized from MeOH to provide the title compound as orange crystals (1.67 g); m.p. 200–202° C. Anal. Calcd. for $C_{17}H_{16}O_5$: C, 67.99; H, 5.37. Found: C, 67.50; H, 5.37.

The following compounds (B–D) were prepared from the appropriate starting material using the above general procedure:

1,2-Dimethoxyfluoren-9-one; m.p. 110–111° C. (EtOAc/cyclohexane). Anal. Calcd. for $C_{15}H_{12}O_3$: C, 75.00; H, 5.04. Found: C, 74.88; H, 4.83.

2,3-Dimethoxyfluoren-9-one; m.p. 158–160° C.

1,2,6,7-Tetramethoxyfluoren-9-one; m.p. 208–209° C. (dioxane/water). Anal. Calcd. for $C_{17}H_{17}O_5$: C, 67.99; H, 5.37. Found: C, 67.77; H, 5.19.

PREPARATION 8

A

N-9H-2,3,6,7-Tetramethoxyfluoren-9-ylidene-(4'-trifluoromethyl)benzamine—To an intimate mixture of 2,3,6,7-tetramethoxyfluoren-9-one (0.60 g, 2.00 mmol) and 4-(trifluoromethyl)benzylamine (0.97 g, 6.00 mmol) under nitrogen was added boron trifluoride etherate (0.2 mL). The resulting dark mixture was heated at 200° C. for 1 hour, cooled and dissolved in a mixture of saturated aqueous sodium bicarbonate/EtOAc. The organic phase was washed with brine, dried ($Na_2SO_4$), filtered and concentrated in vacuo. The resulting solids were recrystallized from methanol to afford the title compound as yellow crystals (0.20 g); m.p. 207–209° C. Anal. Calcd. for $C_{24}H_{20}F_3NO_4$: C, 65.00; H, 4.55; N, 3.16. Found: C, 64.83; H, 4.25; N, 3.01.

The following compounds (B–H) were prepared from the appropriate starting material using the above general procedure:

N-9H-2,3,6,7-Tetramethoxyfluoren-9-ylidene-benzamine; m.p. 191–192° C. Anal. Calcd. for $C_{23}H_{21}NO_4$: C, 73.58; H, 5.64; N. 3.73. Found: C, 72.66; H, 5.56; N, 3.62.

N-9H-2,3,67-Tetramethoxyfluoren-9-ylidene-(4'-cyano)benzamine; m.p. 266–269° C. Anal. Calcd. for $C_{24}H_{20}N_2O_4$: C, 71.98; H, 5.03; N, 7.00. Found: C, 70.53; H, 4.71; N, 6.73.

N-9H-1-Hydroxy-2,6,7-trimethoxyfluoren-9-ylidene-benzamine; m.p. 175–176° C. (MeOH). Anal. Calcd. for $C_{22}H_{19}NO_4$: C, 73.11; H, 5.30; N, 3.88. Found: C, 72.75; H, 4.92; N, 3.71.

N-9H-1-Hydroxy-2,6,7-trimethoxyfluoren-9-ylidene-(3,5-dichloro)benzamine; m.p. 201–203° C. Anal. Calcd. for $C_{22}H_{17}Cl_2NO_4$: C, 61.42; H, 3.98; N, 3.26. Found: C, 61.33; H, 3.92; N, 3.22.

N-9H-1-Hydroxy-2,6,7-trimethoxyfluoren-9-ylidene-(4'-nitro)benzamine; m.p. 211–215° C. Anal. Calcd. for $C_{22}H_{18}N_2O_6$: C, 65.02; H, 4.46; N, 6.89. Found: C, 64.70; H, 4.40; N, 6.64.

N-9H-1-Hydroxy-2,6,7-trimethoxyfluoren-9-ylidene-(4'-i-propyl)benzamine; m.p. 184–185° C. (EtOAc/hexanes). Anal. Calcd. for $C_{25}H_{25}NO_4$: C, 74.43; H, 6.25; N, 3.47. Found: C, 74.36; H, 6.17; N, 3.49.

N-9H-1-Hydroxy-2,6,7-trimethoxyfluoren-9-ylidene-(4'-methylsulfonyl)benzamine; m.p. 203–205° C. (acetone/hexanes). Anal. Calcd. for $C_{23}H_{21}NO_6S$: C, 62.86; H, 4.82; N, 3.19. Found: C, 62.37; H, 4.82; N, 3.22.

PREPARATION 9

A 2,3,6,7-Tetramethoxy-9H-fluorene—A slurry of 2,3,6,7,-tetramethoxy-fluoren-9-one (1.33 g, 4.43 mmol) and 10% palladium-on-carbon (0.4 g) was shaken on a Parr apparatus under 50 psi hydrogen pressure for 24 hours. Hot acetone (50 mL) was added and the reaction mixture was filtered through Celite, washing with several portions of hot acetone. The combined filtrates were concentrated in vacuo and the resulting solids were titrated with MeOH to afford the title compound as gray solid (1.15 g); m.p. 193–195° C. Anal. Calcd. for $C_{17}H_{18}O_4$: C, 71.31; H, 6.34. Found: C, 71.01; H, 6.32.

The following compounds (B–C) were prepared from the appropriate starting material using the above general procedure:

1,2-Dimethoxy-9H-fluorene; m.p. 99–101° C.

2,3-Dimethoxy-9H-fluorene; $^1$H-NMR ($d_6$-DMSO) delta 7.78 (d, 1H), 7.52–7.46 (m, 2H), 7.31 (dd, 1H), 7.22–7.14 (m, 2H).

PREPARATION 10

1,2,6,7-Tetramethoxy-9H-fluorene—To a cooled (0° C.), stirred slurry of 1,2,6,7-Tetramethoxy-fluoren-9-one (6.7 g, 22 mmol) in THF (45 mL) was added a 1M solution of lithium aluminum hydride (22 mL, 22 mmol) in THF over a 5 minute period. The resulting solution was stirred at room temperature for 1 hour, recooled to 0° C., quenched with water (4 mL) and 1N NaOH (0.6 mL). The resulting solids were filtered and washed with hot acetone. The combined filtrates were concentrated in vacuo to a yellow solid. These solids (8.6 g) were dissolved in a 1:1 mixture (200 mL) of THP and acetic acid, 10% palladium-on-carbon (8.6 g) was added and the resulting slurry was shaken on a Parr apparatur under 45 psi hydrogen pressure for 4 hours. The reaction mixture was filtered through Celite, washed with acetone and the combined filtrates were concentrated in vacuo. The resulting solids were recrystallized from acetone/hexane to afford the title compound (4.7 g); m.p. 170–172° C. Anal. Calcd. for $C_{17}H_{18}O_4$: C, 71.31; H, 6.34. Found: C, 70.70; H, 6.37.

PREPARATION 11

A 9-(((4-Trifluoromethyl)phenyl)methylene)-2,3,6,7-tetramethoxyfluorene—To a cooled (0° C.), stirred slurry of 2,3,6,7-tetramethoxy-9H-fluorene (0.50 g, 1.75 mmol) in pyridine (1.5 mL) was added Triton B (40% in MeOH, 0.05 mL) and a solution of 4-(trifluoromethyl)benzaldehyde (0.46 g, 2.62 mmol) in pyridine (1.5 mL). The reaction mixture was allowed to stir at room temperature for 36 hours, additional portions of 4-(trifluoromethyl)benzaldehyde (0.2 g, 0.9 mmol) and Triton B (0.05 mL) were added. The reaction mixture was heated at 60° C. for 18 hours, cooled and IS diluted into EtOAc. This mixture was washed with water, brine, dried ($Na_2SO_4$), filtered and concentrated in vacuo. Flash chromatography (30% acetone/hexane) of the residue afforded the title compound (0.56 g) as an orange solid; m.p. 163–165° C. Anal. Calcd. for $C_{25}H_{21}F_3O_4$: C, 67.87; H, 4.79. Found: C, 67.55; H, 4.56.

The following compounds (B–H) were prepared from the appropriate starting material using the procedure detailed above:

9-(Phenylmethylene)-1,2-dimethoxyfluorene; m.p. 106–110° C.

9-((4-Quinolyl)methylene-1,2-dimethoxyfluorene; m.p. 210° C. (acetone/cyclohexane). Anal. Calcd. for $C_{25}H_{19}NO_2$: C, 82.17; H, 5.24; N, 3.83. Found: C, 82.23; H, 5.00; N, 3.88.

9-(Phenylmethylene)-2,3,6,7-tetramethoxyfluorene; foam. $^1$H-NMR ($d_6$-DMSO) delta 7.62 (s, 1H), 7.55 (d, 2H), 7.51–7.42 (m, 3H), 7.41–7.32 (m, 3H), 6.83 (s, 1H), 3.84 (s, 3H), 3.82 (s, 6H), 3.42 (s, 3H).

9-((4-Methoxyphenyl)methylene)-2,3,6,7-tetramethoxyfluorene; m.p. 179–180° C. Anal. Calcd. for $C_{25}H_{24}O_5$: C, 74.24; H, 5.98. Found: C, 73.95; H, 5.84.

9-((4-Quinolyl)methylene)-2,3,6,7-tetramethoxyfluorene; m.p. 226–228° C. (acetone/cyclohexane). Anal. Calcd. for $C_{27}H_{23}NO_4$:

9-((4-Methoxyphenyl)methylene)-1,2,6,7-tetramethoxyfluorene; m.p. 138–140° C. (EtOAc/hexanes). Anal. Calcd. for $C_{25}H_{24}O_5$: C, 74.24; H, 5.98. Found: C, 73.85; H, 5.88.

9-((4-Quinolyl)methylene)-1,2,6,7-tetramethoxyfluorene; m.p. 203–205° C. (acetone/cyclohexane). Anal. Calcd. for $C_{27}H_{23}NO_4$: C, 76.23; H, 5.45; N, 3.29. Found: C, 75.66; H, 5.13; N, 3.24.

PREPARATION 12

A 9-((4-Methoxyphenyl)methyl)-2,3,6,7-tetramethoxyfluorene—A slurry of 9-((4-Methoxyphenyl)methylene)-2,3,6,7-tetramethoxyfluorene (0.35 g, 0.89 mmol) and 10% palladium-on-carbon (0.04 g) in THF (5 mL) were shaken in a Parr apparatus under 50 psi of hydrogen for 4 hours. The reaction mixture was filtered through Celite, washed with acetone and the filtrates were concentrated in vacuo. The residue was flash chromatographed (30% acetone/hexanes) to afford the title compound (0.33 g); m.p. 168–169° C. (MeOH). Anal. Calcd. for $C_{25}H_{26}O_5$: C, 73.88; H, 6.45. Found: C, 73.89; H, 6.35.

The following compounds (B–G) were prepared from the appropriate starting material using the procedure described above:

9-(Phenylmethyl)-1,2-dimethoxyfluorene; m.p. 93–96° C. Anal. Calcd. for $C_{22}H_{20}O_2$: C, 83.36; H, 6.32.

9-(Phenylmethyl)-2,3,6,7-tetramethoxyfluorene; m.p. 143–144° C. (EtOAc/hexanes). Anal. Calcd. for $C_{24}H_{24}O_4$: C, 76.58; H, 6.43. Found: C, 75.95; H, 6.35.

9-(Phenylmethyl)-1,2,6,7-tetramethoxyfluorene; foam. $^1$H-NMR ($d_6$-DMSO) delta 7.36 (d, 1H), 7.27 (s, 1H), 7.20–7.07 (m, 3H), 7.06–6.97 (m, 3H), 6.49 (s, 1H), 4.28 (dd, 1H), 3.96 (s, 3H), 3.87 (s, 3H), 3.80 (s, 3H), 3.73 (dd, 1H), 3.58 (s, 3H), 2.80 (dd, 1H).

9-((4-Pyridyl)methyl)-2,3,6,7-tetramethoxyfluorene; m.p. 169–171° C. (acetone/hexanes). Anal. Calcd. for $C_{23}H_{23}NO_4$: C, 73.20; H, 6.14; N, 3.71. Found: C, 72.81; H, 6.15; N, 3.67.

9-((4-Quinolyl)methyl)-1,2-dimethoxyfluorene; m.p. 114–116° C. (EtOAc/hexanes). Anal. Calcd. for $C_{25}H_{21}NO_2$: C, 81.72; H, 5.76; N, 3.81. Found: C, 81.60; H, 5.55; N, 3.76.

9-((4-Quinolyl)methyl)-2,3,6,7-tetramethoxyfluorene; m.p. 176–179° C.

PREPARATION 13

A 1,2,6,7-Tetramethoxy-9H-carbazole/2,3,6,7-Tetramethoxy-9H-carbazole—A stirred solution of 2-((3,4-dimethoxy)phenyl)-4,5,-dimethoxynitrobenzene (6.5 g, 20 mmol) in triethylphosphite (10.5 mL, 6.11 mmol) was heated at 160° C. under a nitrogen atmosphere for 10 hours. The excess triethylphosphite was removed in vacuo, residue was slurried in chloroform the solids were filtered and recrystallized from EtOAc to afford 2,3,6,7-tetramethoxy-9H-carbazole (1.9 g); m.p. 232–233° C. Anal. Calcd. for $C_{16}H_{17}NO_4$: C, 66.88; H, 5.97; N, 4.88. Found: C, 65.04; H, 5.62; N, 4.71. The chloroform filtrate from above was concentrated in vacuo and flash chromatographed (20% EtOAc/$CCl_4$) to afford 1,2,6,7-tetramethoxy-9H-carbazole (1.7 g); m.p. 170–171° C. (MeOH). Anal. Calcd. for $C_{16}H_{17}NO_4$: C, 66.88; H, 5.97; N, 4.88. Found: C, 66.75; H, 5.80; N, 4.88.

The following compounds (B) were prepared from the appropriate starting material using the above general procedure:

2,3-Dimethoxy-9H-carbazole; m.p. 188–189° C.

PREPARATION 14

2-((2-Bromo-4,5-dimethoxy)phenyl)-4,5-dimethoxynitrobenzene—To a stirred solution of 2-((3,4-dimethoxy)phenyl)-4,5-dimethoxynitrobenzene (0.5 g, 1.6 mmol) and sodium acetate (0.3 g, 4.0 mmol) in nitromethane (6 mL) was added a solution of bromine (0.5 g, 3.1 mmol) in glacial acetic acid (0.5 mL). After 1 hour, the reaction solution was poured into saturated aqueous sodium bicarbonate and extracted with EtOAc. The organic layer was washed with water, brine, dried ($Na_2SO_4$), filtered and concentrated in vacuo to afford the title compound (0.6 g); m.p. 172–174° C. Anal. Calcd. for $C_{16}H_{16}BrNO_6$: C, 48.25; H, 4.05; N, 3.52. Found: C, 48.24; H, 3.93; N, 3.47.

PREPARATION 15

4-Bromo-1,2,6,7-tetramethoxy-9H-carbazole—A stirred solution of 2-((2-bromo-4,5-dimethoxy)phenyl)-4,5-dimethoxynitrobenzene (0.54 g, 1.37 mmol) in triethylphosphite was heated at 160° C. for 10 hours. The excess triethylphosphite was removed in vacuo and the residue was recrystallized from EtOAc to afford the title compound (0.19 g); m.p. 206–207° C. Anal. Calcd. for $C_{16}H_{16}BrNO_4$: C, 52.47; H, 4.40; N, 3.83. Found: C, 53.07; H, 4.11; N, 3.93.

PREPARATION 16

A 9-(phenylmethyl)-2,3,6,7-tetramethoxycarbazole—To a stirred solution 2,3,6,7-tetramethoxy-9H-carbazole (0.6 g, 2.0 mmol) in anhydrous dimethylsulfoxide (5 mL) was added sodium hydride (60% in oil, 0.16 g, 4.0 mmol). After 0.5 hour, benzyl bromide (2.0 g, 12 mmol) was added, the reaction mixture was stirred for 1 hour, diluted into water and extracted into EtOAc. The organic layer was washed with water, brine, dried ($Na_2SO_4$), filtered and concentrated in vacuo. The residue was flash chromatographed (14% EtOAc/$CCl_4$) to afford the title compound (0.7 g); m.p. 174–176° C. Anal. Calcd for $C_{23}H_{23}NO_4$: C, 73.19; H, 6.14; N, 3.71. Found: C, 73.06; H, 5.83; N, 3.66.

The following compounds (B–Z and AA–AH) were prepared from the appropriate starting material using the above general procedure:

9-Benzoyl-2,3-dimethoxycarbazole; m.p. 155–157° C.

9-Benzoyl-1,2,6,7-tetramethoxycarbazole; m.p. 184–185° C. (MeOH). Anal. Calcd. for $C_{23}H_{21}NO_5$: C, 70.57; H, 5.41; N, 3.58. Found: C, 70.37; H, 5.25; N, 3.49.

9-Benzoyl-2,3,6,7-tetramethoxycarbazole; m.p. 181–182° C. (MeOH). Anal. Calcd. for $C_{23}H_{21}NO_5$: C, 70.57; H, 5.41; N, 3.58. Found: C, 70.17; H, 5.35; N, 3.53.

9-(Phenylmethyl)-1,2,6,7-tetramethoxycarbazole; m.p. 174–175° C. (MeOH). Anal. Calcd. for $C_{23}H_{23}NO_4$: C, 73.19; H, 6.14; N, 3.71. Found: C, 73.06; H, 6.07; N, 3.66.

9-Methyl-2,3,6,7-tetramethoxycarbazole; m.p. 203–205° C. Anal. Calcd. for $C_{17}H_{19}NO_4$: C, 67.76; H, 6.36; N, 4.65. Found: C, 67.62; H, 6.19; N, 4.52.

9-(Methylsulfonyl)-1,2,6,7-tetramethoxycarbazole; m.p. 164–165° C. (MeOH). Anal. Calcd. for $C_{17}H_{19}NO_6S$: C, 55.88; H, 5.24; N, 3.83. Found: C, 55.40; H, 5.43; N, 3.49.

9-(Methylsulfonyl)-2,3,6,7-tetramethoxycarbazole; m.p. 207–210° C. Anal. Calcd. for $C_{17}H_{19}NO_6S$: C, 55.88; H. 5.24; N, 3.83. Found: C, 55.46; H, 5.11; N, 3.80.

9-(Phenylsulfonyl)-1,2,6,7-tetramethoxycarbazole; m.p. 205–206° C. (MeOH). Anal. Calcd. for $C_{22}H_{21}NO_6S$: C, 61.81; H, 4.95; N, 3.28. Found: C, 61.87; H, 4.96; N, 3.11.

9-(Phenylsulfonyl)-2,3,6,7-tetramethoxycarbazole; m.p. 212–213° C. (MeOH). Anal. Calcd. for $C_{22}H_{21}NO_6S$: C, 61.81; H, 4.95; N. 3.28. Found: C, 61.62; H, 4.79; N, 3.25.

9-(4-t-Butylbenzoyl)-1,2,6,7-tetramethoxycarbazole; m.p. 129–131° C. (MeOH). Anal. Calcd. for $C_{27}H_{29}NO_5$: C, 72.46; H, 6.53; N, 3.13. Found: C, 72.28; H, 6.55; N, 3.11.

9-((4-Trifluoromethyl)benzoy)-1,2,6,7-tetramethoxycarbazole; m.p. 124–125° C. (MeOH). Anal. Calcd. for $C_{24}H_{20}F_3NO_5$: C, 62.74; H, 4.39; N, 3.05. Found: C, 62.85;; H, 4.16; N, 2.95.

9-((4-Methylsulfonyl)benzoyl)-1,2,6,7-tetramethoxycarbazole; m.p. 171–172° C. (MeOH). Anal. Calcd. for $C_{24}H_{23}NO_7S$: C, 61.39; H, 4.94; N, 2.98. Found: C, 61.58; H, 4.80; N, 2.90.

9-(4-Bromobenzoyl)-1,2,6,7-tetramethoxycarbazole; 157–158° C. (MeOH). Anal. Calcd. for $C_{23}H_{20}BrNO_5.0.25H_2O$: C, 58.17; H, 4.35; N, 2.95. Found: C, 58.05; H, 4.23; N, 2.92.

9-(4-Phenylbenzoyl)-1,2,6,7-tetramethoxycarbazole: m.p. 150–153° C. (MeOH). Anal. Calcd. for $C_{29}H_{25}NO_5$: C, 74.50; H, 5.39; N, 3.00. Found: C, 74.61; H, 5.07; N, 2.98.

9-(3-Phenylpropionyl)-1,2,6,7-tetramethoxycarbazole; m.p. 106–108° C. (MeOH). Anal. Calcd. for $C_{25}H_{25}NO_5$: C, 71.58; H, 6.01; N, 3.34. Found: C, 71.57; H, 5.78; N, 3.23.

9-(2-Napthoyl)-1,2,6,7-tetramethoxycarbazole; m.p. 137–141° C. (MeOH). Anal. Calcd for $C_{27}H_{23}NO_5$: C, 73.45; H, 5.25; N, 3.17. Found: C, 73.47; H, 4.89; N, 3.15.

9-(3-Nitrobenzoyl)-1,2,6,7-tetramethoxycarbazole; m.p. 187–191° C. (MeOH). Anal. Calcd. for $C_{23}H_{20}N_2O_7$: C, 63.30; H, 4.62; N, 6.42. Found: C, 62.98; H, 4.39; N, 6.42.

9-(3-Pyridylmethyl)-2,3,6,7-tetramethoxycarbazole; m.p. 183–184° C. Anal. Calcd. for $C_{22}H_{22}N_2O_4$: C, 69.82; H, 5.86; N, 7.40. Found: C, 69.40; H, 5.74; N, 7.27.

9-((3-Methylphenyl)methyl)-1,2,6,7-tetramethoxycarbazole; m.p. 145–146° C. Anal. Calcd. for $C_{24}H_{25}NO_4$: C, 73.63; H, 6.44; N, 3.58. Found: C, 73.63; H, 6.28; N, 3.61.

9-((4-Cyanophenyl)methyl)-1,2,6,7-tetramethoxycarbazole; m.p. 147–148° C. (MeOH). Anal. Calcd. for $C_{24}H_{22}N_2O_4$: C, 71.62; H, 5.51; N, 6.96. Found: C, 71.53; H, 5.43; N, 6.95.

9-((4-Trifluoromethylphenyl)methyl)-1,2,6,7-tetramethoxycarbazole; m.p. 145–146° C. (MeOH). Anal. Calcd. for $C_{24}H_{22}F_3NO_4.0.5H_2O$: C, 63.42; H, 5.10; N, 3.08. Found: C, 63.73; H, 4.96; N, 3.12.

9-((2,6-Dichlorophenyl)methyl)-1,2,6,7-tetramethoxycarbazole; m.p. 207–210° C. ($CH_2Cl_2$/MeOH). Anal. Calcd. for $C_{23}H_{21}Cl_2NO_4$: C, 61.89; H, 6.74; N, 3.14. Found: C, 61.58; H, 4.70; N, 3.12.

9-((4-Phenylsulfonyl)phenylmethyl)-1,2,6,7-tetramethoxycarbazole; m.p. 155–157° C. (MeOH). Anal. Calcd. for $C_{29}H_{27}NO_6S$: C, 67.29; H, 5.26; N, 2.71. Found: C, 67.26; H, 5.07; N, 2.70.

9-(4-Bromophenylmethyl)-1,2,6,7-tetramethoxycarbazole; m.p. 143–144° C. ($CH_2Cl_2$/MeOH). Anal. Calcd. for C, 60.53; H, 4.86; N, 3.07. Found: C, 60.55; H, 4.67; N, 2.98.

9-(3-Phenylpropyl)-1,2,6,7-tetramethoxycarbazole; m.p. 116–118° C. (MeOH). Anal. Calcd. for $C_{25}H_{27}NO_4.0.25H_2O$: C, 73.23; H, 6.76; N, 3.46. Found: C, 73.42; H, 6.71; N, 3.42.

9-((Phenylmethyl)sulfonyl)-1,2,6,7-tetramethoxycarbazole; m.p. 152–156° C.

9-((2,5-Dichlorophenyl)sulfonyl)-1,2,6,7-tetramethoxycarbazole; m.p. 221–224° C. ($CH_2Cl_2$).

9-((4-Nitrophenyl)sulfonyl)-1,2,6,7-tetramethoxycarbazole; m.p. 188–189° C. (MeOH). Anal. Calcd. for $C_{22}H_{20}N_2O_8S$: C, 55.92; H, 4.27; N, 5.93. Found: C, 55.91; H, 4.02; N, 5.84.

9-((4-Trifluoromethyl)benzoyl)-4-bromo-1,2,6,7-tetramethoxycarbazole; m.p. 167–168.5° C. (MeOH). Anal. Calcd. for $C_{24}H_{19}BrF_3NO_5$: C, 53.54; H, 3.56; N, 2.60. Found: C, 53.63; H, 3.40; N, 2.57.

9-((4-Methylsulfonyl)benzoyl)-4-bromo-1,2,6,7-tetramethoxycarbazole; m.p. 227–229° C. (MeOH). $C_{24}H_{22}BrNO_7S.0.5H_2O$: C, 51.71; H, 4.16; N, 2.55. Found: C, 51.98; H, 3.79; N, 2.46.

9-(4-t-Butylbenzoyl)-4-bromo-1,2,6,7-tetramethoxycarbazole; m.p. 136–138° C. (MeOH). Anal. Calcd. for C, 61.60; H, 5.36; N, 2.66. Found: C, 62.12; H, 5.46; N, 2.61.

9-((4-Cyanophenyl)methyl)-4-bromo-1,2,6,7-tetramethoxycarbazole; m.p. 162–163° C. Anal. Calcd. for $C_{24}H_{21}BrN_2O_4$: C, 59.88; H, 4.40; N, 5.82. Found: C, 59.89; H, 4.21; N, 5.77.

9-(Methylsulfonyl)-4-bromo-1,2,6,7-tetramethoxycarbazole; m.p. 178–179° C. (MeOH). Anal. Calcd. for $C_{17}H_{18}BrNO_6S$: C, 45.95; H, 4.08; N, 3.15. Found: C, 45.87; H, 3.99; N, 3.13.

It should be understood that the invention is not limited to the particular embodiments shown and described herein, but that various changes and modifications may be made without departing from the spirit and scope of this novel concept as defined by the following claims.

What is claimed is:

1. A compound of formula I

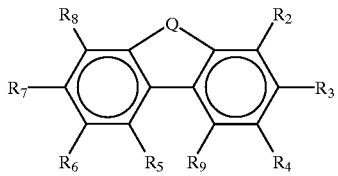

Formula I wherein

Q is

at least three and no more than four of $R_2$, $R_3$, $R_4$, $R_5$, $R_6$, $R_7$, and $R_8$ are OH, the remainder being H;

$R_9$ is H or halo;

$Z_1$ is H, benzyl, alkyl($C_1$–$C_4$), —$(CH_2)_n$—phenyl—$R_{22}$, —$(CH_2)_n$—dichlorophenyl,

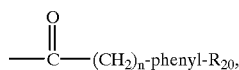

—$SO_2$—$R_{21}$, —$CH_2$—pyridyl or

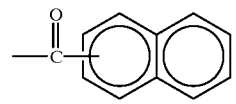

wherein n is 0–3;

$R_{20}$ is H, t-butyl, $CF_3$, —$SO_2$—alkyl($C_1$–$C_4$), halo, alkyl ($C_1$–$C_4$), phenyl or $NO_2$;

$R_{21}$ is phenyl, alkyl($C_1$–$C_4$), benzyl, nitrophenyl, dichlorophenyl or halophenyl;

$R_{22}$ is —C≡N, $CF_3$, phenylsulfonyl, halo or alkyl ($C_1$–$C_4$); and the pharmaceutically-acceptable cationic salts and prodrugs thereof.

2. A compound as recited in claim 1 wherein $R_2$, $R_3$ and $R_4$ are H or OH; $R_6$ and $R_7$ are OH; $R_5$ and $R_8$ are H; $R_9$ is H or halo;

Q is

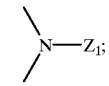

$Z_1$ is H, benzyl, alkyl($C_1$–$C_4$), —$(CH_2)_n$—phenyl—$R_{22}$, —$(CH_2)_n$—dichlorophenyl,

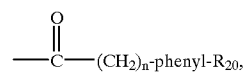

—$SO_2$—$R_{21}$, —$CH_2$—pyridyl and

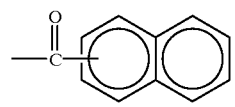

wherein n is 0–3;

$R_{20}$ is H, t-butyl, $CF_3$, —$SO_2$—alkyl($C_1$–$C_4$), halo, alkyl ($C_1$–$C_4$), phenyl or $NO_2$;

$R_{21}$ is phenyl, alkyl($C_1$–$C_4$), benzyl, nitrophenyl, dichlorophenyl or halophenyl; and $R_{22}$ is —C≡N, $CF_3$, phenylsulfonyl, halo or alkyl ($C_1$–$C_4$).

3. A compound as recited in claim 2 wherein $R_2$, $R_3$, $R_6$ and $R_7$ are OH; $R_5$ and $R_8$ are H; and $R_9$ is H or halo.

4. A compound as recited in claim 2 wherein $R_3$, $R_4$, $R_6$, $R_7$ are OH; $R_2$, $R_5$, $R_8$ and $R_9$ are H; and $Z_1$ is H,

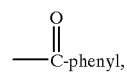

benzyl, —alkyl($C_1$–$C_4$), —$SO_2$—phenyl, —$SO_2$—alkyl ($C_1$–$C_4$) and —$CH_2$—3-pyridyl.

* * * * *